United States Patent [19]

Crivello et al.

[11] 4,238,394

[45] Dec. 9, 1980

[54] METHOD FOR MAKING DIARYLIODONIUM SALTS

[75] Inventors: James V. Crivello, Clifton Park; Julia H. W. Lam, Schenectady, both of N.Y.

[73] Assignee: General Electric Company, Schenectady, N.Y.

[21] Appl. No.: 956,024

[22] Filed: Oct. 30, 1978

Related U.S. Application Data

[62] Division of Ser. No. 749,116, Dec. 9, 1976, Pat. No. 4,151,175.

[51] Int. Cl.$^3$ .............................. C07F 9/68; C07F 9/02; C07F 9/22
[52] U.S. Cl. ........................... 260/326.26; 260/429 R; 260/446; 260/447; 546/1; 546/3; 546/9; 568/931; 260/440; 570/182
[58] Field of Search ............... 260/326.26, 649 DP, 260/646, 300, 299, 429 R, 440, 446, 447; 546/1, 260/465.4; 568/22; 568/23; 560/17;

[56] References Cited

U.S. PATENT DOCUMENTS

| | | | |
|---|---|---|---|
| 3,729,313 | 4/1973 | Smith | 96/27 R |
| 3,808,006 | 4/1974 | Smith | 96/88 |
| 4,151,175 | 4/1979 | Crivello et al. | 260/326.26 |

OTHER PUBLICATIONS

Beringer et al., J.A.C.S., vol. 81, pp. 342-351, (1959).
Berry et al., Twelvth Intl. Cong. Pure and App. Chem., N.Y., N.Y. (9/51) p.465.
Masson et al.; J. Chem. Soc. (London), (1937), pp. 1718-1723.
Masson; Nature, vol. 139, pp. 150-151, (1937).
Caserio et al., J.A.C.S., vol. 81, (1959) pp. 336-342.
Masson et al., J. Chem. Soc. (1938), pp. 1099-1701.

*Primary Examiner*—Mary Lee
*Attorney, Agent, or Firm*—William A. Teoli; James C. Davis, Jr.

[57] ABSTRACT

A method is provided for making certain diaryliodonium salt photoinitiators, based on the initial formation of a diaryliodonium bisulfate. Methylene chloride is substituted for acetic acid during the reaction between potassium iodate and benzene in the presence of acetic anhydride and sulfuric acid. The diaryliodonium bisulfate is then reacted with a counterion source, such as a metal salt, to produce the desired diaryliodonium salt which can be used as a photoinitiator. The iodonium salt photoinitiators made by the method of the present invention can be used to make UV curable compositions.

5 Claims, No Drawings

METHOD FOR MAKING DIARYLIODONIUM SALTS

This is a division of application Ser. No. 749,116, filed Dec. 9, 1976 now U.S. Pat. No. 4,151,175.

The present invention is directed to a method for making diaryliodonium salt photoinitiators. More particularly, the present invention relates to the use of methylene chloride as a solvent in place of acetic acid in forming a diaryliodonium bisulfate reaction intermediate.

Prior to the present invention, as shown by Crivello U.S. Pat. No. 3,981,897, assigned to the same assignee as the present invention, certain halonium salt photoinitiators, such as diaryliodonium hexafluoroarsenates, were prepared by initially forming a diaryliodonium bisulfate of the formula, $$[(R)_a(R^1)_bI]^+[HSO_4]^-, \quad (1)$$

followed by reacting the diaryliodonium bisulfate with a hexafluoro compound, such as potassium hexafluoroarsenate, where R is a monovalent aromatic organic radical, $R^1$ is a divalent aromatic organic radical, a is a whole number equal to 0 or 2, b is a whole number equal to 0 or 1, and the sum of a+b is equal to 2, or the valence of I.

The above described method of Crivello U.S. Pat. No. 3,981,897 can be used to produce a variety of diarylhlaonium hexafluoro salt photoinitiators, but the procedure can involve 16 hours or more of reaction time. In addition, product yields are often difficult to predict because the results are frequently not reproducible. As shown by Crivello, a principal step in the preparation of the photoinitiator is based on the prior formation of the intermediate diarylhalonium bisulfate salt of formula (1). A method for making these diaryliodonium bisulfate slats shown by D. A. Berry et al, Twelfth International Congress, Pure and Applied Chemistry, New York, N.Y., September 1951, page 465. The Berry et al method involves the direct coupling of benzene with iodyl sulfate which can be generated by potassium iodate in the presence of a mixture of acetic acid, acetic anhydride and sulfuric acid. The Berry et al method, based on the use of acetic acid-acetic anhydride and sulfuric acid has been found to require long reaction times and often results in low yields and is difficult to reproduce.

The present invention is based on the discovery that a significant improvement in reproducibility and reduced reaction time as well as higher yields can be achieved with the procedure for making diaryliodonium bisulfate salts of formula (1), hereinafter referred to as the "bisulfate salts", if the acetic acid used in the reaction mixture is replaced with methylene chloride. The improved results achieved with the use of methylene chloride in place of acetic acid in the synthesis of the bisulfate salts can be achieved if the reaction is run at a temperature of from about −25° C. to +25° C., and preferably −5° C. to +5° C.

There is provided by the present invention, a method for making the bisulfate salts of formula (1) which comprises (A) effecting a coupling reaction at a temperature of from −25° C. to +25° C. between a $C_{(6-30)}$ aromatic compound and potassium iodate in the presence of a mixture consisting essentially of methylene chloride, acetic anhydride and sulfuric acid, and (B) recovering the diaryliodonium bisulfate salt from the mixture of (A).

The bisulfate salt can be reacted with a metal salt of the formula, $$MQ, \quad (2)$$

to produce by a metathesis, a diaryliodonium salt of the formula, $$[(R)_a(R^1)_bI]^+[Q]^-, \quad (3)$$

where R, $R^1$, a and b are as previously defined and Q is an anion, such as a halogen ion, for example, chloride, bromide, fluoride, iodide, etc, $YF_6$, where Y is selected from a Group Va element such as P, As and Sb, $NO_3^-$, $ClO_4^{31}$, $CF_3SO_3^{31}$, $PO_4^{-3}$, $SO_4^=$, $HSO_4^-$, $CH_3C_6H_5SO_3^-$, etc. The diaryliodonium salts of formula (3) can be used as photoinitiators as shown by the above Crivello U.S. Pat. No. 3,981,897, Smith U.S. Pat. Nos. 3,729,313, 3,808,006, etc.

Radicals included by R can be the same or different aromatic carbocyclic or heterocyclic radicals having from 6-20 carbon atoms, which can be substituted with from 1-5 monovalent radicals selected from $C_{(1-8)}$ alkoxy, $C_{(1-8)}$ alkyl, nitro, chloro, etc., R is more particularly, phenyl, chlorophenyl, nitrophenyl, methoxyphenyl, pyridyl, etc. Radicals included by $R^1$ are divalent radicals, such as

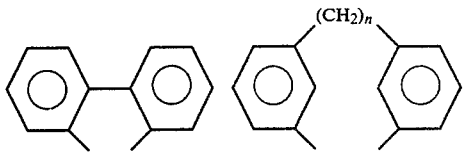

etc.

Some of the bisulfate salts of formula (1) are, for example, diphenyliodonium bisulfate, 4,4'-dichlorodiphenyliodonium bisulfate, 4,4'-dibromodiphenyliodonium bisulfate, 3,3'-dinitrodiphenyliodonium bisulfate, 4,4'-dimehtyldiphenyliodonium bisulfate, 4,4'-bis-succinimidodiphenyliodonium bisulfate, 3,3'-dinitrodiphenyliodonium bisulfate, 4,4'-dimethoxydiphenyliodonium bisulfate.

Included by the Group Va metal hexafluoride salts of formula (2) are, for example, $NaPF_6$, $NaAsF_6$, $KSbF_6$, $KAsF_6$, $Ca(PF_6)_2$, $Mg(AsF_6)_2$, $HPF_6$, $HAsF_6$, $HSbF_6$, $Ba(AsF_6)_2$, $Pb(PF_6)_2$, $Zn(AsF_6)_2$, etc.

Included by the diaryliodonium salts of formula (3) are, for example, compounds such as

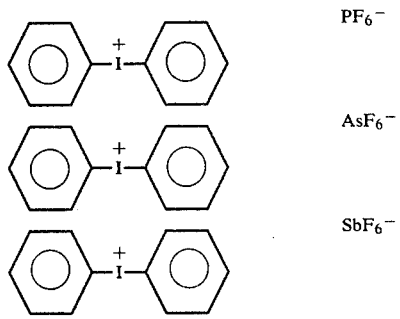

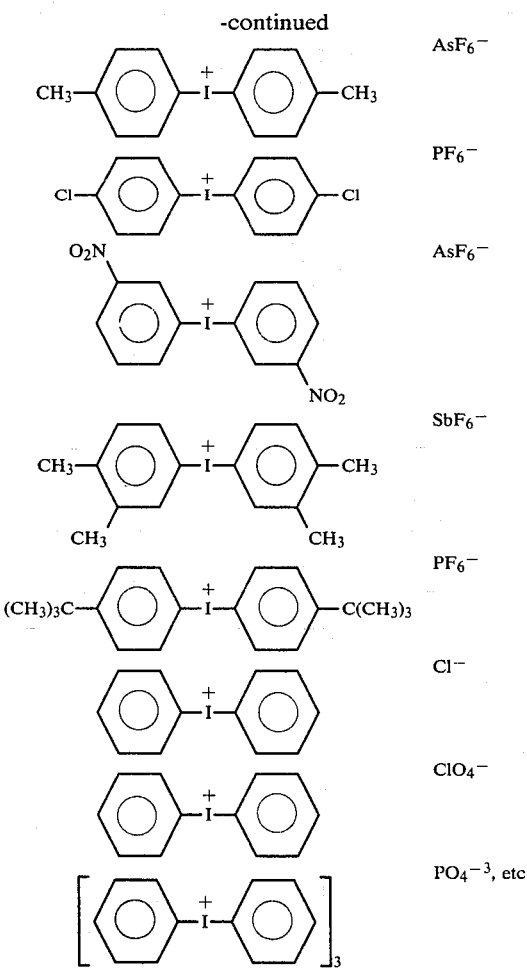

In the practice of the invention, the iodonium bisulfate salt is initially formed by agitating a mixture of aromatic compound, potassium iodate, methylene chloride, sulfuric acid and acetic anhydride. Suitable aromatic compounds include, for example, benzene, toluene, o-xylene, m-xylene, p-xylene, chlorobenzene, bromobenzene, alkylbenzene, nitrobenzene, N-phenylmaleimide.

It has been found that substantially two moles of the aromatic compound to one mole of potassium iodate will provide for effective results. However, a proportion of from 6 moles to 2 moles of aromatic compound per mole of potassium iodate can be used. Sulfuric acid, methylene chloride and acetic anhydride can be employed in excess amounts, while the sulfuric acid is preferably utilized at from 1 mole to 3 moles of sulfuric acid per mole of potassium iodate. The solids concentration of the mixture can vary from 10% to 50% by weight.

After the bisulfate salt has been formed, it can be recovered from the mixture. Alternatively, water can be added to the mixture to dissolve the potassium bisulfate without separating the bisulfate salt. An aqueous solution of the metal salt of formula (2) can then be added directly to the mixture with stirring, resulting in the formation of the diaryliodonium metal salt. The diaryliodonium metal salt can be recovered as a precipitate from the mixture and thereafter filtered, washed and dried by standard techniques.

In order that those skilled in the art will be better able to practice the invention, the following examples are given by way of illustration and not by way of limitation. All parts are by weight.

EXAMPLE 1

There was added 25 parts of concentrated sulfuric acid in a dropwise manner to a mixture of 25 parts of potassium iodate, about 32 parts of benzene, about 50 parts of acetic anhydride and about 115 parts of methylene chloride. The mixture was maintained at a temperature of 0°–5° C. for 1.5 hours and then stirred at room temperature for 4 hours. Fifty parts of distilled water was then added to the mixture to dissolve potassium bisulfate, followed by the addition of 27 parts of potassium hexafluoroarsenate dissolved in 100 parts of water. The mixture was then stirred for 2 hours resulting in the precipitation of a product. The product was filtered and washed with hexane. The salt was then dried at 50° C. in vacuo. There was obtained 34.6 parts or a 63.5% yield of porduct. Based on method of preparation, the product was diphenyliodonium hexafluoroarsenate.

A 3% mixture of the above hexafluoroarsenate salt in 4-vinylcyclohexene oxide is irradiated for 0.5 minutes under a G.E. H3T7 mercury arc ultraviolet lamp. There is obtained a cured tack-free film.

The above procedure is repeated, except that in place of the methylene chloride, there is used 115 parts of acetic acid. In addition, the sulfuric acid is added to the mixture dissolved in acetic anhydride. The mixture was stirred at around 5° C. for 4 hours. The mixture was then filtered. There was added 200 parts of distilled water to the filtrate, followed by 200 parts of diethylether. The aqueous layer was then separated and extracted with diethylether. There was then added to the aqueous solution, 26 parts of potassium hexafluoroarsenate. The mixture was stirred for 2 hours. A white precipitate was obtained which was filtered and washed with water and dried in vacuo. There was obtained 24 parts of diphenyliodonium hexafluoroarsenate representing a 30% yield.

The above procedure employing acetic acid was repeated, except that the reaction mixture was stirred at around 5° C. for 18 hours, instead of 4 hours. There was obtained about a 63% yield of the diphenyliodonium hexafluoroarsenate.

The above results show that the method of the present invention provides a more rapid procedure for making diarylhalonium hexafluoro salts as shown by formula (3). The method of the present invention provided a yield of about 63% after a reaction period of about 6 hours. However, when the same reaction was repeated, except that the acetic acid was substituted for methylene chloride, the yield was reduced to 30%. It required a total reaction time of about 18 hours to obtain a yield which was comparable to that provided by the method of the present invention which was achieved in approximately one-third of the time.

EXAMPLE 2

There were added 45.5 parts of concentrated sulfuric acid to a stirred mixture at 0° C. consisting of 25 parts of potassium iodate, 35 parts of toluene, 149 parts of methylene chloride and 54 parts of acetic anhydride. Addition of the sulfuric acid required 0.5 hours. The reaction was allowed to proceed at 0° C. for four hours. After this period, 50 parts of water were added to dissolve the potassium bisulfate followed by the addition of 27 parts of potassium hexafluoroarsenate in 100 parts of water. This two-phase mixture was allowed to stir for 2 hours. The methylene chloride layer was removed and diluted with 133 parts hexane resulting in the precipitation of 24.8 parts representing a 43% yield of 4,4'-dimethyldiphenyliodonium hexafluoroarsenate. The structure of the compound was identified on the basis of its melting point, 166°–167° C., and by its ultraviolet and nuclear magnetic resonance spectrum.

EXAMPLE 3

Following the procedure of Example 1, 25 parts of potassium iodate, 45 parts of N-phenylmaleimide, 160 parts of methylene chloride and 54 parts of acetic anhydride were combined. To this reaction mixture there were added slowly with vigorous stirring, 45 parts of concentrated sulfuric acid over the course of 0.5 hours while maintaining the temperature below 5° C. The reaction mixture was held at this temperature for 4 hours. Fifty parts of water were then added to dissolve the potassium bisulfate. On addition of the water, rapid precipitation of a yellow product occurred which was filtered and washed with ether. The product, obtained in a 72% yield, was determined on the basis of its nuclear magnetic resonance spectrum and its analysis to be 4,4'-bis-N-phenylmaleimidoiodonium bisulfate,

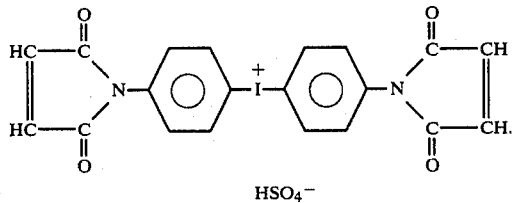

A solution of 10 parts of ammonium chloride in 20 parts of water was added to an aqueous solution of 20 parts of the above iodonium bisulfate. An immediate precipitate of 4,4'-bis-N-phenylmaleimidoiodonium chloride was obtained.

EXAMPLE 4

A mixture of 25 parts of potassium iodate, 39 parts of t-butyl benzene, 54 parts of acetic anhydride and 153 parts of methylene chloride was stirred and cooled to 0° C. There were added slowly, 46 parts of concentrated sulfuric acid to maintain the reaction temperature below 0° C. After completing the addition, the reaction temperature was maintained at 0° C. for 1–1.5 hours and then allowed to stir at room temperature for 3.5 hours. The total reaction time was 4–5 hours. Fifty parts of distilled water was added to dissolve the potassium bisulfate. There was then added 21.5 parts of potassium hexafluorophosphate. After stirring for 15 minutes, the methylene chloride solution is separated from the mixture and the product is triturated with ethylether. The salt is filtered and dried in vacuo to give 33.2 parts or a 52.7% yield of di(p-t-butylphenyl)iodonium hexafluorophosphate.

EXAMPLE 5

A mixture of 25 parts of potassium iodate, 40 parts of o-xylene, 54 parts of acetic anhydride, and 153 parts of methylene chloride was stirred and cooled to 0° C. There were slowly added 46 parts of concentrated sulfuric acid to maintain the reaction temperature below 0° C. After completing the addition, the reaction was maintained at 0° C. for 1–1.5 hours. The mixture was stirred at room temperature for an additional 3.5 hours. The total reaction time was 4–5 hours. Then 50 parts of distilled water was added to dissolve the potassium bisulfate. There was then added 21.5 parts of potassium hexafluorophosphate in about 250 parts of water. After stirring 15 minutes, the methylene chloride layer is separated and the product is triturated with ethylether. The salt is filtered and dried in vacuo to give 27.9 parts or a 49.2% yield of di(3,4-dimethylphenyl)iodonium hexafluorophosphate.

Although the above examples are limited to only a few of the very many variables useful in the practice of the method of the present invention, it should be understood that the present invention is directed to the preparation of a much broader class of diaryliodonium salt photoinitiators as shown in the description preceding these examples.

What we claim as new and desire to secure by Letters Patent of the United States is:

1. In the method of making diaryliodonium salts of the formula $$[(R)_a(R^1)_bI]^+[Q]^-,$$

where R is a monovalent aromatic organic radical, $R^1$ is a divalent aromatic organic radical, a is a whole number equal to 0 or 2, b is a whole number equal to 0 or 1, and the sum of a+b is equal to 2 or the valence of I, Q is an anion selected from the class consisting of halogen ions, $YF_6^-$, $NO_3^{-3}$, $ClO_4^-$, $CF_3SO_3^-$, $PO_4^{-3}$, $SO_4^=$, $HSO_4^-$, $CH_3C_6H_5SO_3^-$, Y is selected from the group consisting of P, As, and Sb, by effecting a metathesis between a metal salt of the formula, $$MQ,$$

where M is a metal ion, and a diaryliodonium bisulfate of the formula, $$[(R)_a(R^1)_bI]^+[HSO_4]^-,$$

which is made by effecting a coupling reaction between a C(6–30) aromatic compound and potassium iodate in the presence of a mixture consisting essentially of acetic acid, acetic anhydride, and sulfuric acid, whereby long reaction times of 16 hours or more are required and product yields are difficult to predict, the improvement which comprises substituting methylene chloride for the acetic acid in the coupling reaction mixture to produce an acetic acid-free mixture during the coupling reaction which is conducted at a temperature of from −25° C. to +25° C., whereby improved yields and reduced reaction time is achieved in the formation of the diaryliodonium bisulfate salt and in the resulting diaryliodonium salt resulting from the metathesis between said metal salt and said diaryliodonium bisulfate salt.

2. The method of claim 1, where Q is $YF_6$.
3. The method of claim 2, where Y is arsenic.
4. The method of claim 2, where Y is phosphorous.
5. The method of claim 1, where Q is chloride.

* * * * *